US008383567B2

(12) United States Patent
Cervin

(10) Patent No.: US 8,383,567 B2
(45) Date of Patent: Feb. 26, 2013

(54) CELLULASE-FREE ENZYME COMPOSITIONS AND HOST CELLS FOR PRODUCING THE SAME

(75) Inventor: Marguerite A. Cervin, Redwood City, CA (US)

(73) Assignee: Danisco US Inc., Palo Alto, CA (US)

( * ) Notice: Subject to any disclaimer, the term of this patent is extended or adjusted under 35 U.S.C. 154(b) by 368 days.

(21) Appl. No.: 12/443,241

(22) PCT Filed: Sep. 26, 2007

(86) PCT No.: PCT/US2007/020851
§ 371 (c)(1),
(2), (4) Date: Dec. 22, 2010

(87) PCT Pub. No.: WO2008/045214
PCT Pub. Date: Apr. 17, 2008

(65) Prior Publication Data
US 2011/0098207 A1    Apr. 28, 2011

Related U.S. Application Data

(60) Provisional application No. 60/849,982, filed on Oct. 6, 2006.

(51) Int. Cl.
C11D 3/386    (2006.01)
C12N 9/50    (2006.01)
(52) U.S. Cl. .................. 510/300; 536/23.2; 435/69.1
(58) Field of Classification Search ............. 510/300; 435/69.1; 536/23.2
See application file for complete search history.

(56) References Cited

U.S. PATENT DOCUMENTS

| 6,509,181 | B1 * | 1/2003 | Danielsen et al. ............ 435/192 |
| 6,511,371 | B2 * | 1/2003 | Outtrup et al. ................ 435/219 |
| 6,511,835 | B1 * | 1/2003 | Danielsen et al. ............ 435/192 |
| 6,521,434 | B2 * | 2/2003 | Danielsen et al. ............ 435/192 |
| 6,524,827 | B2 * | 2/2003 | Moller et al. .................. 435/74 |
| 6,608,018 | B1 * | 8/2003 | Shinohara ...................... 510/392 |
| 7,279,315 | B2 * | 10/2007 | Fukuyama ..................... 435/193 |
| 7,329,527 | B2 * | 2/2008 | Estell ............................. 435/212 |
| 7,919,271 | B2 * | 4/2011 | Shinohara ...................... 435/69.1 |
| 2002/0009435 | A1 * | 1/2002 | Schneider et al. ............ 424/94.4 |
| 2002/0183506 | A1 * | 12/2002 | Danielsen et al. ............ 536/23.2 |

OTHER PUBLICATIONS

International Search Report for PCT/US2007/020851 mailed Apr. 28, 2008, 2 pp.
Kim, Ji-Yeon. "Overproduction and secretion of *Bacillus circulans* endo-beta-1,3-1,4-glucanase gene (*bgIBC1*) in *B. subtilis* and *B. megaterium*," Biotechnology Letters 25:1445-1449, 2003.

(Continued)

*Primary Examiner* — Gregory Webb
(74) *Attorney, Agent, or Firm* — Danisco US Inc.

(57) ABSTRACT

The present invention provides recombinant bacterial cells for producing a detergent-additive protein. In some embodiments, the cells are of the genus *Bacillus*. In additional embodiments, the cells comprise a genome comprising an inactivated bglC gene, as well as a recombinant nucleic acid for production of at least one secreted detergent-additive protein. In some preferred embodiments, the secreted detergent-additive protein is a protease. The present invention also provides methods of using the bacterial cells to produce at least one detergent-additive protein, as well as cellulase-free compositions containing at least one detergent-additive protein.

20 Claims, 3 Drawing Sheets

OTHER PUBLICATIONS

Qureshy et al. "Expression of *Bacillus circulans* Teri-42 Xylanase Gene in *Bacillus subtilis*," *Enzyme and Microbial Technology* 27:227-233, 2000.

Setlow et al. "Mechanism of the Hydrolysis of 4-Methylumbelliferyl-beta-D-glucoside by Germinating and Outgrowing Spores of *Bacillus Species*," *J. Appl. Microbiol.* 96:1245-1255, 2004.

Vehmaanpera et al. "Genetic Manipulation of *Bacillus amyloliquefaciens*," *J. Biotechnol.* 19:221-240, 1991.

Waldeck et al. "Targeted Deletion of Genes Encoding Extracellular Enzymes in *Bacillus licheniformis* and the Impact on the Secretion Capability," *J. Biotech.* 130:124-132, 2007.

\* cited by examiner

SEQUENCE LISTING

<160> NUMBER OF SEQ ID NOS: 26

<210> SEQ ID NO 1
<211> LENGTH: 1478
<212> TYPE: DNA
<213> ORGANISM: Bacillus sp.

<400> SEQUENCE: 1

```
atgaaacggt caatctctat ttttattacg tgtttattga ttacgttatt gacaatgggc      60
ggcatgatag cttcgccggc atcagcagca gggacaaaaa cgccagtagc caagaatggc     120
cagcttaata aaggtacac agctcgttaa ccgagacggt aaagcggtac agctgaaggg      180
gatcagttca cacggattgc aatggtatgg agaatatgtc aataaagaca gcttaaaatg     240
gctgagagat gatgggtatc accgtttttcc gtgcagcgat gtatacggca gatggcggtt    300
atattgacaa cccgtccgtg aaaaataaag taaaagaagc ggttgaagcg gcaaaagagc    360
ttgggatata tgtcatcatg atggcatatc ttaaatgacg gtaatccaaa ccaaaataaa     420
gagaaggcaa agaattctt caaggaaatg tcaagccttt acggaaacac gccaaacgtc    480
atttatgaaa ttgcaaacga accaacggga tgtgaactgg aagcgtgata ttaaaccata     540
tgcggaagaa gtgatttcag ttatccgcaa aaatgatcca gacaacatca tcattgtcgg    600
aaccggtaca tggagccagg atgtgaatga tctgcgatga ccagctaaaa gatgcaaacg    660
ttatgtacgc acttcatttt tatgccggca cgcacggcca attttacgg gataaagcaa     720
actatgcact cagcaaagga gcacctattt ttgtgacgag tgggaacaag cgacgcgtct    780
ggcaatggcg gtgtattcct tgatcaatcg agggaatggc tgaaatatct cgacagcaag    840
accattagct gggtgaactg gaatctttct gataagcagg aatatcctcg ctttaaagcc    900
gggggcatct aaaacaggcg gctggcggtt gtcagattta tctgcttcag gaacattcgt    960
tagagaaaac attctcggca ccaaagattc gacgaaggac attcctgaac gccatcaaag   1020
ataaacccac acaggaaaat ggtatttctg tacagtacag agcaggggat gggagtatga   1080
acagcaacca aatccgtccg cagcttcaaa taaaaaataa cggcaatacc acggtgattt    1140
aaagatgtca ctgcccgtta ctggtataaa gcgaaaaaca aaggccaaaa ctttgactgt   1200
gactacgcgc agattggatg cggcaatgtg acacacaagt tgtgacgtt gcataaacca    1260
agcaaggtgc gataccctatc tggaacttgg atttaaaaac ggaacgttgg caccgggagc   1320
aagcacaggg aatattcagc tccgtcttca caatgatgac tggagcaatt atgcacaaag   1380
cggcgatatt ccttttaaa tcaaatacgt ttaaaacaac gaaaaaaatc acattatatg    1440
atcaaggaaa actgatttgg ggaacagaac caaattag                             1478
```

<210> SEQ ID NO 2
<211> LENGTH: 493
<212> TYPE: PRT
<213> ORGANISM: Bacillus sp.

<400> SEQUENCE: 2

```
Met Lys Arg Ser Ile Ser Ile Phe Ile Thr Cys Leu Leu Ile Thr Leu
1               5                   10                  15

Leu Thr Met Gly Gly Met Ile Ala Ser Pro Ser Ala Ala Gly Thr
            20                  25                  30

Lys Thr Pro Val Ala Lys Asn Gly Gln Leu Ser Ile Lys Gly Thr Gln
        35                  40                  45

Leu Val Asn Arg Asp Gly Lys Ala Val Gln Leu Lys Gly Ile Ser Ser
```

```
                50                  55                  60
His Gly Leu Gln Trp Tyr Gly Glu Tyr Val Asn Lys Asp Ser Leu Lys
65                  70                  75                  80

Trp Leu Arg Asp Asp Trp Gly Ile Thr Val Phe Arg Ala Ala Met Tyr
                85                  90                  95

Thr Ala Asp Gly Gly Tyr Ile Asp Asn Pro Ser Val Lys Asn Lys Val
            100                 105                 110

Lys Glu Ala Val Glu Ala Ala Lys Glu Leu Gly Ile Tyr Val Ile Trp
        115                 120                 125

His Ile Leu Asn Asp Gly Asn Pro Asn Gln Asn Lys Glu Lys Ala Lys
    130                 135                 140

Glu Phe Phe Lys Glu Met Ser Ser Leu Tyr Gly Asn Thr Pro Asn Val
145                 150                 155                 160

Ile Tyr Glu Ile Ala Asn Glu Pro Asn Gly Asp Val Asn Trp Lys Arg
                165                 170                 175

Asp Ile Lys Pro Tyr Ala Glu Glu Val Ile Ser Val Ile Arg Lys Asn
            180                 185                 190

Asp Pro Asp Asn Ile Ile Val Gly Thr Gly Thr Trp Ser Gln Asp
        195                 200                 205

Val Asn Asp Ala Ala Asp Gln Leu Lys Asp Ala Asn Val Met Tyr
    210                 215                 220

Ala Leu His Phe Tyr Ala Gly Thr His Gly Gln Phe Leu Arg Asp Lys
225                 230                 235                 240

Ala Asn Tyr Ala Leu Ser Lys Gly Ala Pro Ile Phe Val Glu Gly Thr
                245                 250                 255

Ser Asp Ala Ser Gly Asn Gly Val Phe Leu Asp Gln Ser Arg Glu
            260                 265                 270

Trp Leu Lys Tyr Leu Asp Ser Lys Thr Ile Ser Trp Val Asn Trp Asn
        275                 280                 285

Leu Ser Asp Lys Gln Glu Ser Ser Ala Leu Lys Pro Gly Ala Ser
    290                 295                 300

Lys Thr Gly Gly Trp Arg Leu Ser Asp Leu Ser Ala Ser Gly Thr Phe
305                 310                 315                 320

Val Arg Glu Asn Ile Leu Gly Thr Lys Asp Ser Thr Lys Asp Ile Pro
                325                 330                 335

Glu Thr Pro Ser Lys Asp Lys Pro Thr Gln Glu Asn Gly Ile Ser Val
            340                 345                 350

Gln Tyr Arg Ala Gly Asp Gly Ser Met Asn Ser Asn Gln Ile Arg Pro
        355                 360                 365

Gln Leu Gln Ile Lys Asn Asn Gly Asn Thr Thr Asp Leu Asp Val Thr
    370                 375                 380

Ala Arg Tyr Trp Tyr Lys Ala Lys Asn Lys Gly Gln Asn Phe Asp Cys
385                 390                 395                 400

Asp Tyr Ala Gln Ile Gly Cys Gly Asn Val Thr His Lys Phe Val Thr
                405                 410                 415

Leu His Lys Pro Lys Gln Gly Ala Asp Thr Tyr Leu Glu Leu Gly Phe
            420                 425                 430

Lys Asn Gly Thr Leu Ala Pro Gly Ala Ser Thr Gly Asn Ile Gln Leu
        435                 440                 445

Arg Leu His Asn Asp Asp Trp Ser Asn Tyr Ala Gln Ser Gly Asp Tyr
    450                 455                 460

Ser Phe Phe Lys Ser Asn Thr Phe Lys Thr Thr Lys Lys Ile Thr Leu
465                 470                 475                 480
```

-continued

Tyr Asp Gln Gly Lys Leu Ile Trp Gly Thr Glu Pro Asn
            485                 490

<210> SEQ ID NO 3
<211> LENGTH: 37
<212> TYPE: DNA
<213> ORGANISM: Artificial
<220> FEATURE:
<223> OTHER INFORMATION: synthetic primer

<400> SEQUENCE: 3
acaaatgagc tcgctggagc attggatggc gcattcc                              37

<210> SEQ ID NO 4
<211> LENGTH: 37
<212> TYPE: DNA
<213> ORGANISM: Artificial
<220> FEATURE:
<223> OTHER INFORMATION: synthetic primer

<400> SEQUENCE: 4
tgatctggat ccccttcgca tcatttggc tctacac                               37

<210> SEQ ID NO 5
<211> LENGTH: 37
<212> TYPE: DNA
<213> ORGANISM: Artificial
<220> FEATURE:
<223> OTHER INFORMATION: synthetic primer

<400> SEQUENCE: 5
aaaactggat ccgggaacag aaccaaatta gttaagc                              37

<210> SEQ ID NO 6
<211> LENGTH: 37
<212> TYPE: DNA
<213> ORGANISM: Artificial
<220> FEATURE:
<223> OTHER INFORMATION: synthetic primer

<400> SEQUENCE: 6
atggtagtcg acgcaaacgc ggctacaata tggctca                              37

<210> SEQ ID NO 7
<211> LENGTH: 25
<212> TYPE: DNA
<213> ORGANISM: Artificial
<220> FEATURE:
<223> OTHER INFORMATION: synthetic primer

<400> SEQUENCE: 7
ttccgcggag ggccggccta ctata                                           25

<210> SEQ ID NO 8
<211> LENGTH: 25
<212> TYPE: DNA
<213> ORGANISM: Artificial
<220> FEATURE:
<223> OTHER INFORMATION: synthetic primer

<400> SEQUENCE: 8
catattcaca atgcgatggt agagg                                           25

<210> SEQ ID NO 9
<211> LENGTH: 25
<212> TYPE: DNA
<213> ORGANISM: Artificial

```
<220> FEATURE:
<223> OTHER INFORMATION: synthetic primer

<400> SEQUENCE: 9
ttatgcacaa agcggcgatt attcc                                          25

<210> SEQ ID NO 10
<211> LENGTH: 22
<212> TYPE: DNA
<213> ORGANISM: Artificial
<220> FEATURE:
<223> OTHER INFORMATION: synthetic primer

<400> SEQUENCE: 10
atctcttgcc agtcacgtta cg                                             22

<210> SEQ ID NO 11
<211> LENGTH: 37
<212> TYPE: DNA
<213> ORGANISM: Artificial
<220> FEATURE:
<223> OTHER INFORMATION: synthetic primer

<400> SEQUENCE: 11
ggagtgtcta gaactgacca gcttccgtct ttccctg                             37

<210> SEQ ID NO 12
<211> LENGTH: 37
<212> TYPE: DNA
<213> ORGANISM: Artificial
<220> FEATURE:
<223> OTHER INFORMATION: synthetic primer

<400> SEQUENCE: 12
actaacggat ccctgtaac tatcatcatc ttccctc                              37

<210> SEQ ID NO 13
<211> LENGTH: 37
<212> TYPE: DNA
<213> ORGANISM: Artificial
<220> FEATURE:
<223> OTHER INFORMATION: synthetic primer

<400> SEQUENCE: 13
caaaaaggat ccgccaaatg tgaaagagcc tgctgca                             37

<210> SEQ ID NO 14
<211> LENGTH: 37
<212> TYPE: DNA
<213> ORGANISM: Artificial
<220> FEATURE:
<223> OTHER INFORMATION: synthetic primer

<400> SEQUENCE: 14
agaggtgagc tcaccgctga ttcccgctat gatcgcc                             37

<210> SEQ ID NO 15
<211> LENGTH: 27
<212> TYPE: DNA
<213> ORGANISM: Artificial
<220> FEATURE:
<223> OTHER INFORMATION: synthetic primer

<400> SEQUENCE: 15
caatatacac aatacagtgc tgaaagc                                        27
```

```
<210> SEQ ID NO 16
<211> LENGTH: 25
<212> TYPE: DNA
<213> ORGANISM: Artificial
<220> FEATURE:
<223> OTHER INFORMATION: synthetic primer

<400> SEQUENCE: 16
gcgggaatag cgatgcttgg ttcgg                                          25

<210> SEQ ID NO 17
<211> LENGTH: 25
<212> TYPE: DNA
<213> ORGANISM: Artificial
<220> FEATURE:
<223> OTHER INFORMATION: synthetic primer

<400> SEQUENCE: 17
gatgaacttg tggaatggca cgggt                                          25

<210> SEQ ID NO 18
<211> LENGTH: 30
<212> TYPE: DNA
<213> ORGANISM: Artificial
<220> FEATURE:
<223> OTHER INFORMATION: synthetic primer

<400> SEQUENCE: 18
tcgacggtat cgataagctg gatccataac                                     30

<210> SEQ ID NO 19
<211> LENGTH: 32
<212> TYPE: DNA
<213> ORGANISM: Artificial
<220> FEATURE:
<223> OTHER INFORMATION: synthetic primer

<400> SEQUENCE: 19
gcctaggatg catatgggat ccgcataact tc                                  32

<210> SEQ ID NO 20
<211> LENGTH: 6
<212> TYPE: DNA
<213> ORGANISM: Artificial
<220> FEATURE:
<223> OTHER INFORMATION: synthetic restriction site

<400> SEQUENCE: 20 tctaga                                                                6

<210> SEQ ID NO 21
<211> LENGTH: 6
<212> TYPE: DNA
<213> ORGANISM: Artificial
<220> FEATURE:
<223> OTHER INFORMATION: synthetic restriction site

<400> SEQUENCE: 21 ggatcc                                                                6

<210> SEQ ID NO 22
<211> LENGTH: 6
<212> TYPE: DNA
<213> ORGANISM: Artificial
<220> FEATURE:
<223> OTHER INFORMATION: synthetic restriction site

<400> SEQUENCE: 22
```

```
gagctc                                                              6

<210> SEQ ID NO 23
<211> LENGTH: 6
<212> TYPE: DNA
<213> ORGANISM: Artificial
<220> FEATURE:
<223> OTHER INFORMATION: synthetic restriction site

<400> SEQUENCE: 23 ggtacc                                                              6

<210> SEQ ID NO 24
<211> LENGTH: 6
<212> TYPE: DNA
<213> ORGANISM: Artificial
<220> FEATURE:
<223> OTHER INFORMATION: synthetic restriction site

<400> SEQUENCE: 24 ctgcag                                                              6

<210> SEQ ID NO 25
<211> LENGTH: 6
<212> TYPE: DNA
<213> ORGANISM: Artificial
<220> FEATURE:
<223> OTHER INFORMATION: synthetic restriction site

<400> SEQUENCE: 25 aagctt                                                              6

<210> SEQ ID NO 26
<211> LENGTH: 4
<212> TYPE: PRT
<213> ORGANISM: Artificial
<220> FEATURE:
<223> OTHER INFORMATION: synthetic reagent
<220> FEATURE:
<221> NAME/KEY: VARIANT
<222> LOCATION: (1)..(2)
<223> OTHER INFORMATION: L-Ala
<220> FEATURE:
<221> NAME/KEY: VARIANT
<222> LOCATION: (3)..(3)
<223> OTHER INFORMATION: L-Pro
<220> FEATURE:
<221> NAME/KEY: VARIANT
<222> LOCATION: (4)..(4)
<223> OTHER INFORMATION: L-Phe

<400> SEQUENCE: 26

Ala Ala Pro Phe
1
```

US 8,383,567 B2

CELLULASE-FREE ENZYME COMPOSITIONS AND HOST CELLS FOR PRODUCING THE SAME

CROSS-REFERENCE TO RELATED APPLICATIONS

This application is a National Stage under 35 U.S.C. §371 of International Application No. PCT/US2007/020851, filed Sep. 26, 2007, which claims the benefit of U.S. Provisional Application No. 60/849,982, filed Oct. 6, 2006, the specifications of which are both hereby incorporated by reference.

FIELD OF THE INVENTION

The present invention provides recombinant bacterial cells for producing a detergent-additive protein. In some embodiments, the cells are of the genus *Bacillus*. In additional embodiments, the cells comprise a genome comprising an inactivated bglC gene, as well as a recombinant nucleic acid for production of at least one secreted detergent-additive protein. In some preferred embodiments, the secreted detergent-additive protein is a protease. The present invention also provides methods of using the bacterial cells to produce at least one detergent-additive protein, as well as cellulase-free compositions containing at least one detergent-additive protein.

BACKGROUND

Expression and recombinant production of exogenous polypeptides is a widely used technique. It is well known that cells can be transformed with nucleic acids encoding exogenous polypeptides of interest for expression and production of large quantities of the desired polypeptides. In some applications, the methods are used to produce vast amounts of polypeptide over what would be produced naturally by the originating organism. Indeed, expression of exogenous nucleic acid sequences, as well as over-expression of endogenous sequences have been extensively used in modern biotechnology.

In some cases, undesirable products are produced along with the protein of interest. For example, in production of a recombinant enzyme (e.g., a protease, amylase or the like), other enzymes that are undesirable (e.g., cellulases) may also be produced.

Despite advances in molecular biology and protein engineering, there remains a need for methods and compositions that reduce, if not eliminate such undesirable activities.

SUMMARY OF THE INVENTION

The present invention provides recombinant bacterial cells for producing a detergent-additive protein. In some embodiments, the cells are of the genus *Bacillus*. In additional embodiments, the cells comprise a genome comprising an inactivated bglC gene, as well as a recombinant nucleic acid for production of at least one secreted detergent-additive protein. In some preferred embodiments, the secreted detergent-additive protein is a protease. The present invention also provides methods of using the bacterial cells to produce at least one detergent-additive protein, as well as cellulase-free compositions containing at least one detergent-additive protein.

The present invention provides recombinant *Bacillus* sp. host cells comprising a genome comprising an inactivated bglC gene, wherein the cell further comprises a recombinant nucleic acid for production of a secreted detergent-additive protein. In some preferred embodiments, the inactivated bglC gene contains a deletion, an insertion, a substitution or a rearrangement. In some alternative preferred embodiments, the *Bacillus* sp. cell is a *B. lichenifonnis, B. subtilis, B. clausii, B. alkalophilus* or *B. halodurans* cell. In still further preferred embodiments, the secreted detergent-additive protein is an enzyme selected from a protease, an amylase, a pectate lyase and a lipase. In some particularly preferred embodiments, the enzyme is a protease. In some more particularly preferred embodiments, the protease is a subtilisin. In yet further preferred embodiments, the bglC gene encodes a polypeptide that is at least 80% identical to SEQ ID NO:2.

The present invention also provides cultures of cells comprising culture medium and a recombinant *Bacillus* sp. host cell comprising a genome comprising an inactivated bglC gene, wherein the cell further comprises a recombinant nucleic acid for production of a secreted detergent-additive protein. In some preferred embodiments, the inactivated bglC gene contains a deletion, an insertion, a substitution or a rearrangement. In some alternative preferred embodiments, the *Bacillus* sp. cell is a *B. lichenifonnis, B. subtilis, B. clausii, B. alkalophilus* or *B. halodurans* cell. In still further preferred embodiments, the secreted detergent-additive protein is an enzyme selected from a protease, an amylase, a pectate lyase, an acyltransferase, an arylesterase and a lipase. In some particularly preferred embodiments, the enzyme is a protease. In some more particularly preferred embodiments, the protease is a subtilisin. In yet further preferred embodiments, the bglC gene encodes a polypeptide that is at least 80% identical to SEQ ID NO:2.

The present invention further provides methods comprising maintaining the culture of cells under conditions suitable to produce the secreted detergent-additive protein. In some embodiments, the methods further comprise recovering the secreted detergent-additive protein from the culture medium. In additional embodiments, the methods further comprise combining the secreted detergent-additive protein with a laundry detergent. In still further preferred embodiments, the detergent-additive protein is a subtilisin protease.

The present invention also provides a cellulase-free protein or enzyme composition produced by the methods set forth herein. In some preferred embodiments, the composition comprises a secreted detergent-additive protein produced by a *Bacillus* sp. and is characterized in that the composition is does not have detectable cellulase activity.

The present invention further provides a cellulase-free laundry detergent comprising a secreted detergent-additive protein produced by the methods set forth herein. In some embodiments, the cellulase-free laundry detergent comprises a cellulosic polymer.

The present invention also provides methods for making a host cell, comprising introducing a first recombinant nucleic acid into a *Bacillus* sp. cell so that the recombinant nucleic acid recombines with the bglC gene of the cell; and introducing a second recombinant nucleic acid into the cell that provides for expression of the secreted detergent-additive protein. In some preferred embodiments, the nucleic acid inserts into the bglC gene. In some alternative preferred embodiments, the nucleic acid deletes at least a portion of the bglC gene. In still further preferred embodiments, the secreted detergent-additive protein is a subtilisin.

BRIEF DESCRIPTION OF THE DRAWINGS

Certain aspects of the following detailed description are best understood when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DESCRIPTION OF THE INVENTION

Figure 1A:
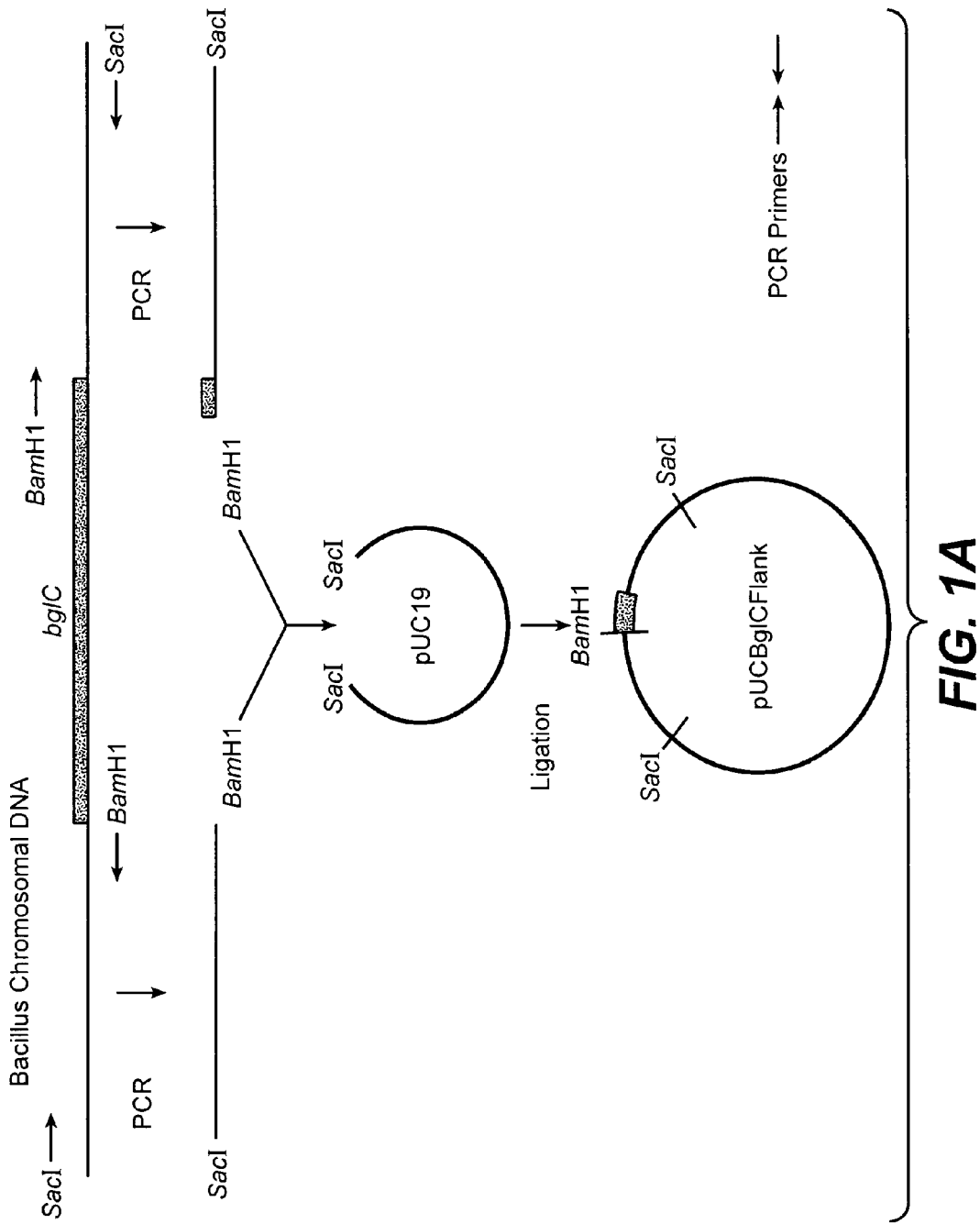
FIGS. 1A-B provide the strategy employed to construct a *Bacillus* host cell containing an inactivated bglC gene.

The present invention provides recombinant bacterial cells for producing a detergent-additive protein. In some embodiments, the cells are of the genus *Bacillus*. In additional embodiments, the cells comprise a genome comprising an inactivated bglC gene, as well as a recombinant nucleic acid for production of at least one secreted detergent-additive protein. In some preferred embodiments, the secreted detergent-additive protein is a protease. The present invention also provides methods of using the bacterial cells to produce at least one detergent-additive protein, as well as cellulase-free compositions containing at least one detergent-additive protein.

Unless otherwise indicated, the practice of the present invention involves conventional techniques commonly used in molecular biology, microbiology, protein purification, protein engineering, protein and DNA sequencing, and recombinant DNA fields, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, NY (1994); and Hale and Marham, The Harper Collins Dictionary of Biology, Harper Perennial, N.Y. (1991) provide those of skill in the art with a general dictionaries of many of the terms used herein. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Thus, for example, reference to a "host cell" includes a plurality of such host cells. Likewise, reference to "a gene" includes a plurality of such candidate agents and reference to "the cell" includes reference to one or more cells and equivalents thereof known to those skilled in the art, and so forth.

Numeric ranges are inclusive of the numbers defining the range. Indeed, it is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein. Where a range of values is provided, it is understood that each intervening value, to the tenth of the unit of the lower limit unless the context clearly dictates otherwise, between the upper and lower limits of that range is also specifically disclosed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All documents cited are, in relevant part, incorporated herein by reference; the citation of any document is not to be construed as an admission that it is prior art with respect to the present invention. Nothing herein is to be construed as an admission that the present invention is not entitled to antedate such publication by virtue of prior invention. All patents and publications, including all sequences disclosed within such patents and publications, referred to herein are expressly incorporated by reference.

Although any suitable methods and materials similar or equivalent to those described herein can be used in the practice or testing of the present invention, exemplary and preferred methods and materials are now described.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention that can be had by reference to the specification as a whole. It is to be understood that this invention is not limited to the particular methodology, protocols, and reagents described, as these may vary, depending upon the context they are used by those of skill in the art. Accordingly, the terms defined immediately below are more fully defined by reference to the Specification as a whole.

As used herein, the term "recombinant" refers to a polynucleotide or polypeptide that does not naturally occur in a host cell. A recombinant molecule may contain two or more naturally-occurring sequences that are linked together in a way that does not occur naturally. A recombinant cell contains a recombinant polynucleotide or polypeptide.

As used herein, the term "heterologous" refers to elements that are not normally associated with each other. For example, if a host cell produces a heterologous protein, that protein that is not normally produced by that host cell. Likewise, a promoter that is operably linked to a heterologous coding sequence is a promoter that is operably linked to a coding sequence that it is not usually operably linked to in a wild-type host cell.

As used herein, he term "homologous," when used in reference to a polynucleotide or protein, refers to a polynucleotide or protein that occurs naturally in a host cell.

The terms "protein" and "polypeptide" are used interchangeably herein.

As used herein, a "signal sequence" is a sequence of amino acids present at the N-terminal portion of a protein which facilitates the secretion of the mature form of the protein outside the cell. The definition of a signal sequence is a functional one. The mature form of the extracellular protein lacks the signal sequence which is cleaved off during the secretion process.

As used herein, a "coding sequence" is a DNA segment that encodes a polypeptide.

As used herein, an "inactivated gene" is a locus of a genome that, prior to its inactivation, was capable of producing a protein (i.e., capable of being transcribed into an RNA that could be translated to produce a full length polypeptide). A gene encoding an enzyme is inactivated when it not transcribed and translated into full length catalytically active protein. A gene may be inactivated by altering a sequence required for its transcription, for example by altering a sequence required for RNA processing (e.g., poly-A tail addition), or by altering a sequence required for translation. Examples of inactivated genes include but are not limited to a deleted gene, a gene containing a deleted region, a gene containing a rearranged region, a gene having an inactivating point mutation or frameshift, and a gene containing an insertion. In addition, a gene may also be inactivated using antisense or any other method that abolishes expression of that gene.

As used herein, the term "nucleic acid" encompasses DNA, RNA, whether single stranded or double stranded, and encompasses chemically modified DNA or RNA. The terms "nucleic acid" and "polynucleotide" are used interchangeably herein.

As used herein, the term "vector" refers to a polynucleotide designed to introduce nucleic acids into one or more host cells. In preferred embodiments, vectors autonomously replicate in different host cells. The term is intended to encompass, but is not limited to cloning vectors, expression vectors, shuttle vectors, plasmids, phage particles, cassettes, and the like.

An "expression vector" as used herein refers to a DNA construct comprising a protein-coding region that is operably linked to a suitable control sequence capable of effecting expression of the protein in a suitable host cell. In some embodiments, such control sequences include a promoter to effect transcription, an optional operator sequence to control transcription to produce mRNA, a sequence encoding suitable ribosome binding sites on the mRNA, and enhancers and sequences which control termination of transcription and translation.

As used herein, the term "promoter" refers to a regulatory sequence that initiates transcription of a downstream nucleic acid.

As used herein, the term "operably linked" refers to an arrangement of elements that allows them to be functionally related. For example, a promoter is operably linked to a coding sequence if it controls the transcription of the sequence.

As used herein, the term "selective marker" refers to a protein capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

As used herein, the term "derived" encompasses the terms "originated from," "obtained," or "obtainable from," and "isolated from".

As used herein, a "non-pathogenic" organism is an organism that is not pathogenic to humans and/or other animals.

The terms "recovered," "isolated," and "separated," as used herein refer to a protein, cell, nucleic acid or amino acid that is removed from at least one component with which it is naturally associated.

As used herein, the terms "transformed," "stably transformed," and "transgenic" when used in reference to a cell means the cell has a non-native (e.g., heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process includes both transcription and translation.

As used herein, the term "introduced" in the context of inserting a nucleic acid sequence into a cell, means "transfection," "transformation," or "transduction," and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the term "hybridization" refers to the process by which a strand of nucleic acid joins with a complementary strand through base pairing as known in the art. A nucleic acid is considered to be "selectively hybridizable" to a reference nucleic acid sequence if the two sequences specifically hybridize to one another under moderate to high stringency hybridization and wash conditions. Moderate and high stringency hybridization conditions are known to those of skill in the art (See e.g., Ausubel et al., *Short Protocols in Molecular Biology,* 3rd ed., Wiley & Sons, Hoboken, N.J. [1995]; and Sambrook et al., *Molecular Cloning: A Laboratory Manual,* 3rd ed., Cold Spring Harbor, N.Y. [2001]). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

As used herein, the term "cellulosic polymer" refers to cellulose, hemicellulose or modified cellulose or hemicellulose polymers that comprise at least one 1,4-beta-D glucosidic linkage.

As used herein, the term "cellulose" refers to a polysaccharide polymer comprising glucose residues joined by beta-1,4 linkages.

As used herein, the term "hemicellulose" refers to a polysaccharide polymer comprising at least one non-glucose saccharide residue (e.g., xylose, galactose, arabinose, rhamnose, mannose, uronic acid or galacturonic acid, or xylans), joined by a beta-(1-4) linkage. Hemicelluloses include xylan, glucuronoxylan, arabinoxylan, arabinogalactan, glucomannan, xyloglucan, and galactomannan.

As used herein, "cellulase" refers to an enzyme that hydrolyzes the 1,4-beta-D-glucosidic linkages in cellulose, lichen and cereal beta-D-glucans. The cellulase described herein has an activity described as EC 3.2.1.4, according to IUMBM enzyme nomenclature. The systematic name for the cellulase described herein is 1,4-(1,3;1,4)-beta-D-glucan 4-glucanohydrolase.

As used herein, the term "*Bacillus* sp." (e.g., a *Bacillus* host cell) refers to any species of the genus *Bacillus* including but not limited to *B. subtilis, B. lichenifonnis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*, as well as subspecies thereof.

As used herein, "cellulase-free *Bacillus* sp." refers to a genetically engineered *Bacillus* sp. host cell that does not secrete a detectable amount of cellulase. As will be discussed in greater detail below, in certain embodiments, a cellulase-free *Bacillus* strain may contain an inactivated bglC gene.

As used herein, an "equivalent unaltered *Bacillus* sp. strain" refers to the host strain that is otherwise identical to a cellulase-free *Bacillus* sp. strain, except the bglC gene is not altered (i.e., is wild-type).

As used herein, "culturing" refers to growing a population of microbial cells under suitable conditions in a liquid or solid medium. In some embodiments, culturing refers to fermentative recombinant production of an exogenous protein of interest or other desired end products (typically in a vessel or reactor).

As used herein, a "detergent-additive protein" refers to a protein that is to be added to laundry detergent. A detergent-additive protein may be an enzyme (e.g., a protease, amylase, pectate lyase, lipase, acyltransferase, arylesterases or a protein that does not have enzymatic activity) In some particularly preferred embodiments, beta-glucan hydrolases (i.e., enzymes having an activity described as EC 3.2.1.8, EC 3.2.1.32, EC 3.2.1.72, EC 3.2.1.136, according to IUMBM enzyme nomenclature), are specifically excluded from the term "detergent-additive protein." In further particularly preferred embodiments, xylanases (i.e., enzymes having an activity described as EC 3.2.1.75, according to IUMBM enzyme nomenclature) are also specifically excluded from the term "detergent-additive protein."

Other definitions of terms may appear throughout the Specification.

Before the exemplary embodiments are described in more detail, it is to be understood that the present invention is not limited to particular embodiments described, as such may, of course, vary. It is also to be understood that the terminology used herein is for the purpose of describing particular embodiments only, and is not intended to be limiting.

Host Cells

As noted above, a *Bacillus* sp. host cell that produces reduced (e.g., undetectable) levels of cellulase is provided by the present invention. In general terms, the subject *Bacillus* sp. host cell typically produces less than about 50% (e.g., less than about 40%, less than about 30%, less than about 20%, or less than about 10%) of the cellulase of an equivalent wild-type *Bacillus* sp. host cell. In some embodiments, the subject cell produces less than about 5% of the cellulase of an equivalent *Bacillus* sp. host cell. In some particularly preferred embodiments, the cellulase is undetectable (i.e., the *Bacillus* sp. host cell is a cellulase-free *Bacillus* sp. host cell). It is intended that cellulase activity be assessed by any suitable method known, for example, by staining cellulose-containing LP agar plates with Congo red (See e.g., Wolf et al, Microbiol., 141:281-290 [1995]; and Carder, Anal. Biochem., 153: 75-9 [1986]), and/or by using a viscosity assay, as described in more detail below.

In some embodiments, a *Bacillus* sp. host cell that produces a reduced amount of cellulase is produced by reducing the expression of the bglC gene product by the cell. In such embodiments, bglC expression is reduced in a *Bacillus* sp. host cell using any suitable method, including but not limited to methods that employ antisense molecules, or ribozymes, for example. In some preferred embodiments, expression of bglC is reduced by inactivating the bglC gene in the cell.

The DNA sequences of several *Bacillus* sp. bglC genes and the proteins encoded by those genes have been determined and deposited in NCBI's Genbank database. The sequence is provided below:

```
                                            (SEQ ID NO: 1)
ATGAAACGGTCAATCTCTATTTTTATTACGTGTTTATTGATTACGTTATT

GACAATGGGCGGCATGATAGCTTCGCCGGCATCAGCAGCAGGGACAAAAA

CGCCAGTAGCCAAGAATGGCCAGCTTAATAAAAGGTACACAGCTCGTTAA

CCGAGACGGTAAAGCGGTACAGCTGAAGGGGATCAGTTCACACGGATTGC

AATGGTATGGAGAATATGTCAATAAAGACAGCTTAAAATGGCTGAGAGAT

GATGGGTATCACCGTTTTCCGTGCAGCGATGTATACGGCAGATGGCGGTT

ATATTGACAACCCGTCCGTGAAAAATAAAGTAAAAGAAGCGGTTGAAGCG

GCAAAAGAGCTTGGGATATATGTCATCATGATGGCATATCTTAAATGACG

GTAATCCAAACCAAAATAAAGAGAAGGCAAAAGAATTCTTCAAGGAAATG

TCAAGCCTTTACGGAAACACGCCAAACGTCATTTATGAAATTGCAAACGA

ACCAACGGGATGTGAACTGGAAGCGTGATATTAAACCATATGCGGAAGAA

GTGATTTCAGTTATCCGCAAAAATGATCCAGACAACATCATCATTGTCGG

AACCGGTACATGGAGCCAGGATGTGAATGATCTGCGATGACCAGCTAAAA

GATGCAAACGTTATGTACGCACTTCATTTTTATGCCGGCACGCACGGCCA

ATTTTTACGGGATAAAGCAAACTATGCACTCAGCAAAGGAGCACCTATTT

TTGTGACGAGTGGGAACAAGCGACGCGTCTGGCAATGGCGGTGTATTCCT

TGATCAATCGAGGGAATGGCTGAAATATCTCGACAGCAAGACCATTAGCT

GGGTGAACTGGAATCTTTCTGATAAGCAGGAATATCCTCGCTTTAAAGCC

GGGGGCATCTAAAACAGGCGGCTGGCGGTTGTCAGATTTATCTGCTTCAG

GAACATTCGTTAGAGAAAACATTCTCGGCACCAAAGATTCGACGAAGGAC

ATTCCTGAACGCCATCAAAGATAAACCCACACAGGAAAATGGTATTTCTG

TACAGTACAGAGCAGGGGATGGGAGTATGAACAGCAACCAAATCCGTCCG

CAGCTTCAAATAAAAATAACGGCAATACCACGGTGATTTAAAGATGTCA

CTGCCCGTTACTGGTATAAAGCGAAAAACAAAGGCCAAAACTTTGACTGT

GACTACGCGCAGATTGGATGCGGCAATGTGACACACAAGTTTGTGACGTT

GCATAAACCAAGCAAGGTGCGATACCTATCTGGAACTTGGATTTAAAAAC

GGAACGTTGGCACCGGGAGCAAGCACAGGGAATATTCAGCTCCGTCTTCA

CAATGATGACTGGAGCAATTATGCACAAAGCGGCGATATTCCTTTTTAAA

TCAAATACGTTTAAAACAACGAAAAAAATCACATTATATGATCAAGGAAA

ACTGATTTGGGGAACAGAACCAAATTAG
```

The following is the amino acid sequence encoded by SEQ ID NO:1.

(SEQ ID NO: 2)
MKRSISIFITCLLITLLTMGGMIASPASAAGTKTPVAKNGQLSIKGTQLV

NRDGKAVQLKGISSHGLQWYGEYVNKDSLKWLRDDWGITVFRAAMYTADG

GYIDNPSVKNKVKEAVEAAKELGIYVIWHILNDGNFNQNKEKAKEFFKEM

SSLYGNTPNVIYEIANEPNGDVNWKRDIKPYAEEVISVIRKNDPDNIIIV

GTGTWSQDVNDAADDQLKDANVMYALHFYAGTHGQFLRDKANYALSKGAP

IFVEGTSDASGNGGVFLDQSREWLKYLDSKTISWVNWNLSDKQESSSALK

PGASKTGGWRLSDLSASGTFVRENILGTKDSTKDIPETPSKDKPTQENGI

SVQYRAGDGSMNSNQIRPQLQIKNNGNTTDLDVTARYWYKAKNKGQNFDC

DYAQIGCGNVTHKFVTLHKPKQGADTYLELGFKNGTLAPGASTGNIQLRL

HNDDWSNYAQSGDYSFFKSNTFKTTKKITLYDQGKLIWGTEPN

Further, several conserved domains of cellulase enzymes have been identified, as well as a number of conserved amino acids, allowing the identification of further *Bacillus* sp. bglC genes and proteins by bioinformatic methods.

In some embodiments, the *Bacillus* sp. bglC gene comprises at least 70% (e.g., at least 80%, at least 90%, at least 95%, at least 97% or at least 98% sequence identity) to a bglC sequence deposited in NCBI's Genbank database and provided above (SEQ ID NO:1). In some further embodiments, the *Bacillus* sp. bglC gene hybridizes under stringent conditions to a bglC sequence deposited in NCBI's Genbank database or SEQ ID NO:1. In yet additional embodiments, the *Bacillus* sp. bglC gene encodes a polypeptide that has at least 70% sequence identity (e.g., at least 80%, at least 90%, at least 93%, at least 95%, at least 97% or at least 98% sequence identity) to a bglC sequence deposited in NCBI's Genbank database or SEQ ID NO:2. Exemplary bglC protein and nucleotide sequences deposited in NCBI's Genbank database include: GID:3100136 (*Bacillus licheniformis*), GID:52348343 (*Bacillus licheniformis*), GID:42491106 (*Bacillus amyloliquefaciens*) and GID:50812243 (*Bacillus subtilis*). The above Genbank accessions are incorporated by reference in their entirety, including the nucleic acid and protein sequences therein and the annotation of those sequences.

In some preferred embodiments, the *Bacillus* sp. host cell is of any of the following species: *B. licheniformis, B. lentus, B. subtilis, B. amyloliquefaciens, B. brevis, B. stearothermophilus, B. alkalophilus, B. coagulans, B. circulans, B. pumilus, B. thuringiensis, B. clausii,* or *B. megaterium*. *B. subtilis* host cells include, but not limited to those described in U.S. Pat. Nos. 5,264,366 and 4,760,025 (RE 34,606), as well as 1A6 (ATCC 39085), 168 (1A01), SB19, W23, Ts85, B637, PB1753 through PB1758, PB3360, JH642, 1A243 (ATCC 39,087), ATCC 21332, ATCC 6051, MI113, DE100 (ATCC 39,094), GX4931, PBT 110, and PEP 211 strain (See e.g., Hoch et al., Genetics 73:215-228 [1973]; U.S. Pat. Nos. 4,450,235; 4,302,544; and EP 0134048 (See also, Palva et al., Gene 19:81-87 [1982]; and Fahnestock and Fischer, J. Bacteriol., 165:796-804 [1986]; and Wang et al., Gene 69:39-47 [1988]).

In some embodiments, the host cell comprises a recombinant nucleic acid comprising an expression cassette (i.e., a promoter, a polynucleotide encoding a detergent-additive protein, and a transcriptional terminator), wherein the expression cassette is sufficient for the production of the detergent-additive protein by the *Bacillus* sp. host cell. In some embodiments, the recombinant nucleic acid is integrated into the genome of the host cell, while in other embodiments, the recombinant nucleic acid is present in a vector that replicates autonomously from the genome. In some embodiments, the polynucleotide encoding the detergent-additive protein is codon optimized for expression of the protein in the *Bacillus* sp. host cell.

In some particularly preferred embodiments, the *Bacillus* host cell is engineered to maximize protein expression. Thus, in some embodiments, the host cells contain an inactivating alteration in at least one of the following genes, degU, degS, degR and/or degQ (See, Msadek et al., J. Bacteriol., 172:824-834 [1990]; and Olmos et al., Mol. Gen. Genet., 253:562-567 [1997]). In some particularly preferred embodiments, the host cell is a *B. subtilis* that carries a degU32(Hy) mutation. In some additional embodiments, the *Bacillus* host cell comprises a mutation and/or deletion in scoC4, (See, Caldwell et al., J. Bacteriol. 183:7329-7340 [2001]); spoIIE (See, Arigoni et al., Mol. Microbiol., 31:1407-1415 [1999]); oppA or another gene in the opp operon (See, Perego et al., Mol. Microbiol., 5:173-185 [1991]). Indeed, it is contemplated that any mutation in the opp operon that causes the same phenotype as a mutation in the oppA gene will find use in some embodiments of the altered *Bacillus* strain of the present invention. In some embodiments, these mutations occur alone, while in other embodiments, combinations of mutations are present. In some embodiments, an altered *Bacillus* of the invention is obtained from a *Bacillus* host strain that already includes a mutation to one or more of the above-mentioned genes. In alternate embodiments, an altered *Bacillus* of the invention is further engineered to include mutation of one or more of the above-mentioned genes.

*Bacillus* sp. host cells constructed using any convenient method find use in the present invention, including cells constructed by altering the sequence of the bglC gene of the cell by making an insertion, deletion, replacement, frameshift, point mutation, and/or rearrangement in the gene find use in the present invention. In some embodiments, the portion of the gene to be altered is within the coding region or a regulatory element required for expression of the coding region. In some embodiments, the regulatory or control sequence of a gene is a promoter sequence or a functional part thereof (i.e., a part which is necessary for expression of the gene). Such gene inactivation methods are well known in the art (See e.g., Wolf et al Microbiol., 141:281-290 [1995]).

In some embodiments, the host cell is constructed by: introducing a recombinant nucleic acid into a *Bacillus* sp. cell so that the recombinant nucleic acid recombines with the bglC gene of the cell's genome and introducing a second recombinant nucleic acid into the cell to provide for expression of a secreted detergent-additive protein. In some embodiments, the nucleic acid inserts into the bglC gene, while in other embodiments, it deletes at least a portion of the bglC gene.

Suitable methods for introducing polynucleotide sequences into *Bacillus* cells are well known to those of skill in the art (See e.g., Ferrari et al., "Genetics," in Harwood et al. (ed.), *Bacillus*, Plenum Publishing Corp. [1989], pages 57-72; See also, Saunders et al., J. Bacteriol., 157:718-726 [1984]; Hoch et al., J. Bacteriol., 93:1925-1937 [1967]; Mann et al., Curr. Microbiol., 13:131-135 [1986]; and Holubova, Folia Microbiol., 30:97 [1985]; Chang et al., Mol. Gen. Genet., 168:11-115; [1979]; Vorobjeva et al., FEMS Microbiol. Lett., 7:261-263 [1980]; Smith et al., Appl. Env. Microbiol., 51:634 [1986]; Fisher et al., Arch. Microbiol., 139:213-217 [1981]; and McDonald, J. Gen. Microbiol., 130:203

[1984]). Indeed, such methods as transformation including protoplast transformation and congression, transduction, and protoplast fusion are known and suited for use in the present invention.

As also noted above, in addition to producing reduced (e.g., undetectable) levels of cellulase, the present invention provides a *Bacillus* sp. host cell that further contains a recombinant nucleic acid for production of a secreted detergent-additive protein, where a secreted detergent-additive protein is a protein (e.g., an enzyme) that is secreted from the cell and is added to laundry detergent. Exemplary detergent-additive proteins include, but are not limited to proteases (e.g., subtilisins), alpha-amylases, mannanases, cellulases, lyases, acyltransferases, arylesterases and lipases, etc. In some embodiments, the detergent-additive protein may be expressed by a strain that is the same as the strain from which the detergent-additive protein is derived.

Enzymes

Subtilisins (i.e., extracellular alkaline serine proteases), are of particular interest. Any suitable subtilisin finds use in the present invention (See e.g., Siezen, Protein Sci., 6:501-523 [1997]; Bryan, Biochim. Biophys. Acta, 1543:203-222 [2000]; Maurer, Curr. Op, Biotechnol., 2004 15:330-334 [2004]; and Gupta, Appl. Microbiol. Biotechnol., 59:15-32 [2002]). In some embodiments, the subtilisin of interest has an activity described as EC 3.4.4.16, according to IUMBM enzyme nomenclature.

In some embodiments, such a subtilisin has an amino acid sequences that is found in wild-type genomes (i.e., the subtilisin is a naturally-occurring subtilisin), while in other embodiments, the subtilisin is a variant of a naturally-occurring subtilisin. In some preferred embodiments, the variant subtilisin comprises an amino acid sequence that is at least 80%, at least 90%, at least 95% or at least 98% identical to a subtilisin encoded by a wild-type genome. Exemplary subtilisins include, but are not limited to: ALCANASE® (Novozymes), FNA™ (Genencor), SAVINASE® (Novozymes) PURAFECT™ (Genencor), KAP™ (Kao), EVERLASE™ (Novozymes), PURAFECT OxP™ (Genencor), FN4™ (Genencor), BLAP S™ (Henkel), BLAP X™ (Henkel), ESPERASE® (Novozymes), KANNASE™ (Novozymes) and PROPERASE™ (Genencor). In yet additional embodiments, the subtilisin includes, but is not limited to subtilisin 168, subtilisin BPN', subtilisin Carlsberg, subtilisin DY, subtilisin 147, or subtilisin 309 (See e.g., EP414279B; WO89/06279; and Stahl et al., J. Bacteriol., 159:811-818 [1984]). Additional subtilisins and other proteases that find use in the present invention include but are not limited to those described in WO 99/20770; WO 99/20726; WO 99/20769; WO 89/06279; RE 34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567; and 6,218,165.

Detergents and Detergent-Additive Proteins

In some embodiments, the host cells are used to make protein compositions and laundry detergents, where the detergent, in some preferred embodiments, contains at least one cellulosic polymer.

In some embodiments, the host cell is cultured to provide at least one secreted detergent-additive protein into the growth medium in which the cell is growing. In some particularly preferred embodiments, the secreted detergent-additive protein is recovered from the growth medium using any suitable method (e.g., precipitation, centrifugation, affinity, filtration or any other method known in the art). For example, affinity chromatography (Tilbeurgh et al., FEBS Lett., 16:215 [1984]); ion-exchange chromatographic methods (Goya) et al., Bio. Technol., 36:37 [1991]; Fliess et al., Eur. J. Appl. Microbiol. Biotechnol., 17:314 [1983]; Bhikhabhai et al., J. Appl. Biochem., 6:336 [1984]; and Ellouz et al., Chromatogr., 396:307 [1987]), including ion-exchange using materials with high resolution power (See e.g., Medve et al., J. Chromatogr. A 808:153 [1998]); hydrophobic interaction chromatography (Tomaz and Queiroz, J. Chromatogr. A 865:123 [1999]; two-phase partitioning (Brumbauer et al., Bioseparation 7:287 [1999]); ethanol precipitation; reverse phase HPLC; chromatography on silica or on a cation-exchange resin such as DEAE; chromatofocusing; SDS-PAGE; ammonium sulfate precipitation; and gel filtration (e.g., SEPHADEX® G-75), find use.

In some preferred embodiments, the detergent-additive protein is used without purification from the other components the culture medium. In some of these embodiments, the culture medium is simply concentrated and then used without further purification of the protein from the components of the growth medium. In other embodiments, the culture medium is used without any further modification.

The protein compositions produced using the host cells generally contain reduced cellulose, as compared to an equivalent *Bacillus* host cell that contains an unaltered (e.g., wild-type) bglC gene.

In one embodiment, the cellulase content of a composition is evaluated by measuring the change in viscosity of a solution of a cellulosic polymer (e.g., a solution containing 1% carboxymethyl cellulose (CMC)) upon addition of the composition to the solution. Such methods are well known (See e.g., Manning, Biochem. Biophys. Meth., 5:189-202 [1981]; and Sheperd, Biochem. J., 193:67-74 [1981]). One exemplary viscosity assay that finds use with the present invention is provided in the Examples below.

In some embodiments comprising the protein composition of the present invention, the composition is capable of reducing the viscosity of a solution of cellulosic material by less than 80% (e.g., less than 50%, less than 30%, less than 20% or less than 10%), as compared to the reduction by an equivalent protein composition produced using a *Bacillus* cell having an unaltered bglC gene. In some embodiments, the protein composition does not produce a detectable reduction in the viscosity of a solution of cellulosic material, in which case the protein composition is considered to be a "cellulase-free" protein composition.

Cellulase-free protein compositions find use in various settings, including but not limited to laundry detergents, particularly those detergents that contain cellulosic polymers. In some embodiments, laundry detergents comprising the cellulase-free protein composition of the present invention contain from about 1% to 80%, (e.g., 5% to 50%)(by weight) of surfactant. In some embodiments, the surfactant is a nonionic surfactant, while in other embodiments, it is a cationic surfactant, and in still other embodiments, it is an anionic surfactant, and in further embodiments it is a zwitterionic surfactant, and in still further embodiments, it comprises any mixture thereof (e.g., a mixture of anionic and nonionic surfactants). Exemplary surfactants include, but are not limited to alkyl benzene sulfonate (ABS), including linear alkyl benzene sulfonate and linear alkyl sodium sulfonate, alkyl phenoxy polyethoxy ethanol (e.g., nonyl phenoxy ethoxylate or nonyl phenol), diethanolamine, triethanolamine and monoethanolamine. Additional descriptions of surfactants that find use in laundry detergents are provided in U.S. Pat. Nos. 3,664,961, 3,919,678, 4,222,905, and 4,239,659.

The laundry detergent comprising the cellulase-free enzyme of the present invention finds use in any form (e.g., solid, liquid, gel, etc.). In some embodiments, the laundry detergents further contain a buffer such as sodium carbonate, sodium bicarbonate, or detergent builder, bleach, bleach activator, an enzymes, an enzyme stabilizing agent, suds booster, suppresser, anti-tarnish agent, anti-corrosion agent, soil suspending agent, soil release agent, germicide, pH adjusting agent, non-builder alkalinity source, chelating agent, organic or inorganic filler, solvent, hydrotrope, optical brightener, dye or perfumes.

As noted above, in some embodiments, the laundry detergents contain a cellulosic polymer (e.g., a cellulose polymer) or a modified cellulose polymer. Suitable cellulosic polymers include, but are not limited to anionically modified cellulose, nonionically modified cellulose, cationically modified cellulose, zwitterionically modified cellulose, and mixtures thereof, as well as cellulose, cellulose ethers, cellulose esters, cellulose amides, methyl cellulose, carboxy methyl cellulose, ethyl cellulose, hydroxyl ethyl cellulose, hydroxylpropyl methyl cellulose, ester carboxy methyl cellulose, and any mixture(s) thereof. In some embodiments, a modified cellulose ether polymer (See e.g., U.S. Pat. No. 6,833,347), or other cellulosic polymer (See e.g., U.S. Pat. Nos. 5,009,800 and 4,661,267) find use in the present invention. In some embodiments, the laundry detergent contains from about 0.1% to 8% by weight (e.g., about 0.5% to 4% or about 1% to 3%, of cellulosic polymer).

EXPERIMENTAL

The following examples provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

In the experimental disclosure which follows, the following abbreviations apply: ° C. (degrees Centigrade); rpm (revolutions per minute); $H_2O$ (water); aa (amino acid); by (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); h(s) and hr(s) (hour/hours); $OD_{280}$ (optical density at 280 nm); $OD_{405}$ (optical density at 405 nm); $OD_{600}$ (optical density at 600 nm); PAGE (polyacrylamide gel electrophoresis); LAS (lauryl sodium sulfonate); SDS (sodium dodecyl sulfate); and Tris (tris(hydroxymethyl)aminomethane).

Example 1

Construction of bglC::Spectinomycin Strains

Figure 1B:
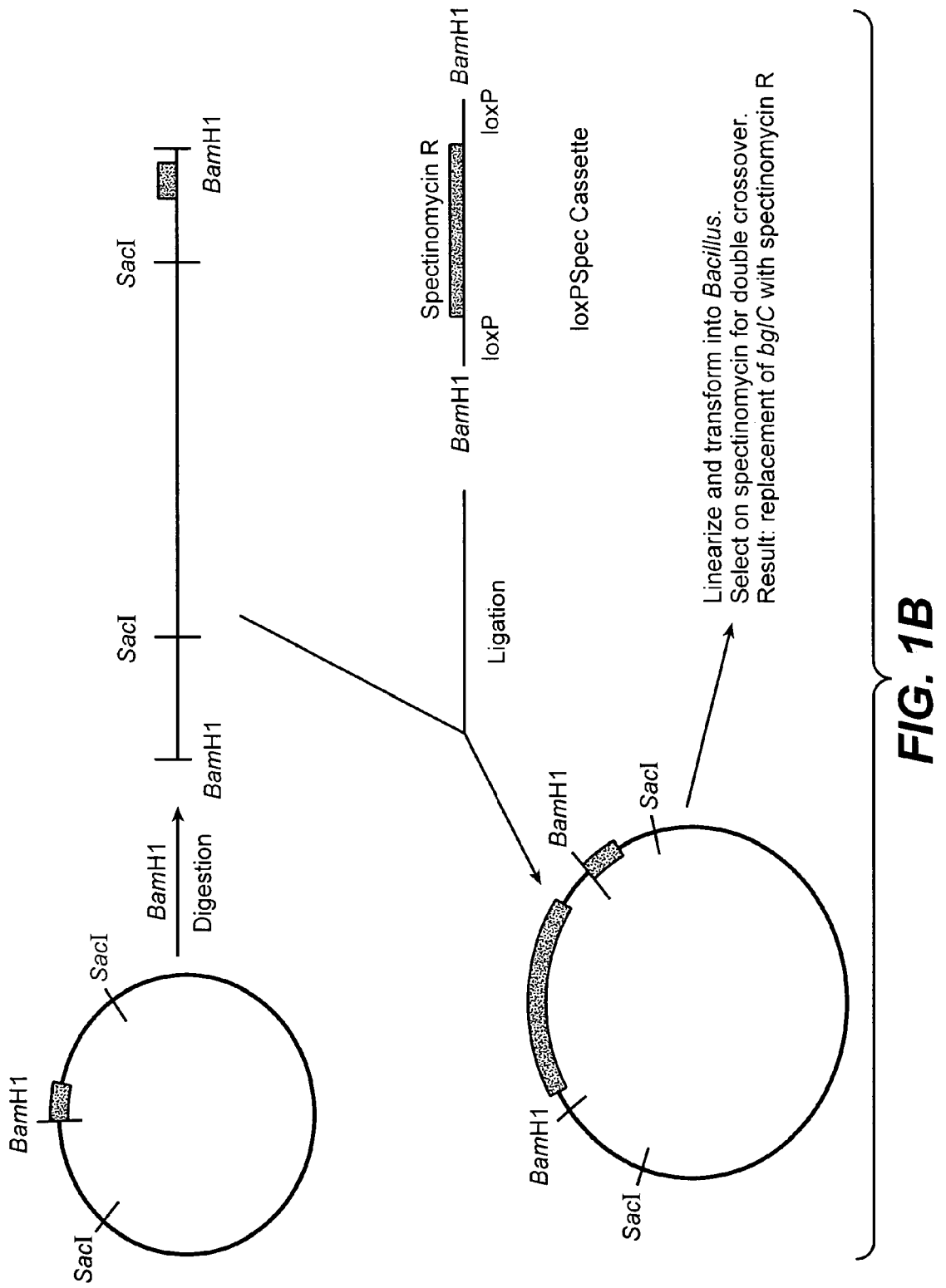

The general strategy for the deletion of the bglC gene is depicted in the diagrams in FIGS. 1A-B. Briefly, upstream and downstream DNA fragments flanking the bglC gene were amplified by PCR and ligated together in a vector. The insert was opened by digestion with a restriction endonuclease and the spectinomycin cassette, flanked by loxP sites, was ligated in. The resultant plasmid was linearized by digestion with a restriction endonuclease and transformed into *Bacillus*. By selection with the introduced antimicrobial marker (spectinomycin), the replacement of the gene of interest was accomplished by a double crossover event. In the case of bglC, the coding region was replaced with the spectinomycin resistance gene that was looped out using the Cre recombinase which recognizes the flanking loxP sites.

DNA constructs were made using PCR technology using the strategy described in WO 03/083125 and the primers described in of Table 1.

TABLE 1

Primers

| Primer Name | Restr. Site in Primer | Primer Sequence | SEQ ID NO: |
|---|---|---|---|
| BglC SacI UF IUF | SacI | acaaatGAGCTCgctggagcattggatggcgcattcc | 3 |
| BglC BamH1 UR | BamH1 | TgatctGGATCCcattcgcatcattttggctctacac | 4 |
| BglC BamH1 DF | BamH1 | AaaactGGATCCgggaacagaaccaaattagttaagc | 5 |
| bglC SalI DR | SalI | atggtaGTCGACgcaaacgcggctacaatatggctca | 6 |
| bglC Uout chk | | ttccgcggagggecggcetactata | 7 |
| bglC Dout chk | | catattcacaatgcgatggtagagg | 8 |
| bglC DF chkdel | | Ttatgcacaaagcggcgattattcc | 9 |
| SPECchkUR: | | Atctcttgccagtcacgttacg | 10 |
| bglS xba UF | Xba | ggagtgTCTAGAactgaccagcttccgtctttccctg | 11 |
| BglS BamH1 UR | BamH1 | ActaacGGATCCcctgtaactatcatcatcttccctc | 12 |
| BglS BamH1 DF | BamH1 | CaaaaaGGATCCgccaaatgtgaaagagcctgctgca | 13 |
| bglS Sac DR | Sac | agaggtGAGCTCaccgctgattcccgctatgatcgcc | 14 |
| bglS Uout chk | | Caatatacacaatacagtgctgaaagc | 15 |

TABLE 1-continued

Primers

| Primer Name | Restr. Site in Primer | Primer Sequence | SEQ ID NO: |
|---|---|---|---|
| bglS Drout chk | | Gcgggaatagcgatgcttggttcgg | 16 |
| bglS DF chk del | | Gatgaacttgtggaatggcacgggt | 17 |
| PloxBamUF | | TCGACGGTATCGATAAGCTGGATCCATAAC | 18 |
| ploxBamDR | | GCCTAGGATGCATATGGGATCCGCATAACTTC | 19 |

The restriction sites are designated as follows: XbaI is TCTAGA (SEQ ID NO:20); BamHI is GGATCC (SEQ ID NO:21); SacI is GAGCTC (SEQ ID NO:22); Asp718 is GGTACC (SEQ ID NO:23); PstI is CTGCAG (SEQ ID NO:24) and HindIII is AAGCTT (SEQ ID NO:25).

In this method, 100 µL PCR reactions were carried out in 150 µL, Eppendorf tubes containing 84 µL water, 10 µL PCR buffer, 1 µL of each primer (i.e., BglC SacI UF and BglC BamHI UR, or loxPBamH1F and loxPBamH1R), 2 µL of dNTPs, 1 µL of DNA template (e.g., wild type Bacillus chromosomal or control plasmid), and 1 µL of DNA polymerase. DNA polymerases used included Taq Plus Precision polymerase and Herculase (Stratagene). Reactions were carried out in a Hybaid PCRExpress thermocycler using the following program. The samples were first heated at 94° C. for 5 minutes, then cooled to a 50° C. hold. The DNA polymerase was added at this point. Twenty-five cycles of amplification consisted of 1 minute at 95° C., 1 minute at 50° C. and 1 minute at 72° C. A final 10 minutes at 72° C. ensured complete elongation. Samples were held at 4° C. until analysis. The reactions yielded the flanking DNA cassettes (approximately 1 kb each) and the loxPspectinomycin cassette with BamHI restriction sites at the 5' and 3' ends.

After completion of the PCR, 10 µL of each reaction were electrophoresed on an Invitrogen 1.2% agarose E-gel at 60 volts for 30 minutes to check for the presence of a band at the correct size. All the gel electrophoresis methods described herein used these conditions. If a band was present, the remainder of the reaction tube was purified using the Qiagen QIAQUICK® PCR purification kit according to the manufacturer's instructions, then cut with the appropriate restriction enzyme pair. Digests were performed at 37° C. for 1 hour as a 20 µL reaction consisting of 9 µL of water, 2 µL of 10×BSA, 2 µL of an appropriate NEB restriction buffer (according to the 2000-01 NEB Catalog and Technical Reference), 5 µL of template, and 1 µL of each restriction enzyme. For example, the bglC upstream fragment was cut with SacI and BamHI in NEB (New England BioLabs) restriction buffer B. The digested fragments were purified by gel electrophoresis and extraction using the Qiagen QIAQUICK® gel extraction kit following the manufacturer's instructions.

Ligation of the fragments into a plasmid vector was done in two steps, using either the Takara ligation kit, following the manufacturer's instructions or T4 DNA ligase (Reaction contents: 5 µL each insert fragment, 1 µL cut pUC19 plasmid, 3 µL T4 DNA ligase buffer, and 1 µL T4 DNA ligase). First, the cut upstream and downstream fragments were ligated overnight at 15° C. into unique restriction sites in the pUC19 plasmid (See, Yanisch-Reman et al., Gene 33:103-119 [1985]) polylinker that had been digested with SacI and gel purified, connecting at the common BamHI site to re-form a circular plasmid. This re-circularized plasmid was transformed into Invitrogen's competent "Top 10" E. coli cells, using the manufacturers One Shot transformation protocol.

Transformants were selected on Luria-Bertani (LB) broth solidified with 1.5% agar (LA) plus 50 ug/ml carbenicillin containing X-gal (Sigma) for blue-white screening. Clones were picked and grown overnight at 37° C. in 5 mL of Luria Bertani broth (LB) plus 50 ug/ml carbenicillin and plasmids were isolated using Qiagen's QIAQUICK® Mini-Prep kit. Restriction analysis using SacI confirmed the presence of the 2 kb insert. Confirmed plasmids with the insert were cut with BamHI to linearize them in digestion reactions as described above (with an additional 1 µL of water in place of a second restriction enzyme), treated with 1 µL calf intestinal or shrimp phosphatases for 1 hour at 37° C. to prevent re-circularization, and ligated to the BamHI digested spectinomycin resistance cassette flanked by loxP sites. This ligation mix was transformed into E. coli Top 10 cells, and colonies were selected on LA plates containing using 100 ug/ml spectinomycin. Confirmation of marker insertion in isolated plasmids was done as described above, by restriction analysis with BamHI. Prior to transformation into B. subtilis, the plasmid was linearized with ScaI to ensure a double crossover event.

Example 2

Viscosity Assay

Cells were grown in 250 ml baffled flasks containing 50 mL of growth media suitable for subtilisin production (See, Christianson et al., Anal. Biochem., 223:119-129 [1994]; and Hsia et al., Anal. Biochem., 242:221-227 [1996]). The media were inoculated with 50 µL of an 8 hour 5 mL culture, and grown for 40 hours at 37° C. with shaking at 250 RPM. Cultures of Host A (-bglC) Host B (-bglC), Host C (-bglS) and Host D (-bglS) were grown for 48 hours.

A 1 ml sample was taken from each shake flask at 37 hours. The cells were removed by centrifugation and 60 microliters of the supernatant were subjected to a viscosity assay. Viscosity was measured at t=0, t=22 hours and t=120 hours. Water was used as the control.

Viscosity was measured using the following method: a 2 ml volume of 1% cellulosic material (carboxymethyl cellulose) was dispensed into cryogenic vials for each experiment. A 60 microliter sample was added to 2 ml volume of cellulosic material. After gently mixing, samples were taken for analysis at the appropriate preselected time (e.g., incubation for 20 hours). For analysis, 500 microliters of sample and substrate were pipetted into a sample cup of a viscometer (Brookfield LV DVIII Cone & Plate viscometer with a CP40 waterbath set at 25° C.) and viscometer was programmed so that the SSN (set speed) was at 16 RPM, and the WTI (wait time) was set at 30 seconds (Rheocalc software). After 30 seconds, a summary sheet was displayed.

Figure 2:
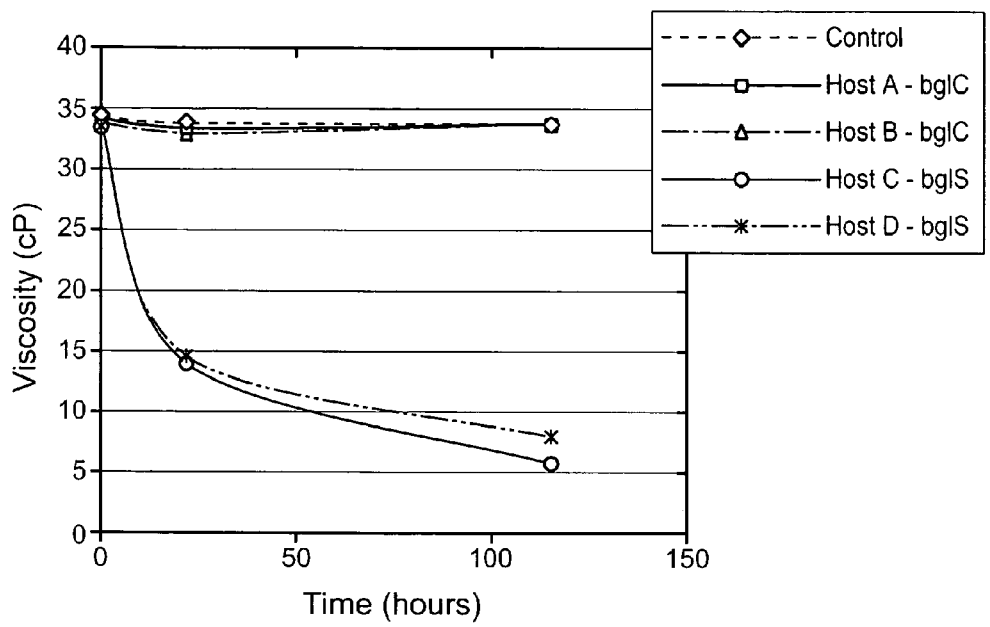
FIG. 2 provides a graph showing the results of viscosity assays on the culture supernatants of two *Bacillus subtilis* strains having an inactivated bglC gene (i.e., "host A" and "host B") and two *Bacillus subtilis* strains having an inactivated bglS genes (i.e., "host C" and "host D"). Fluid viscosity is measured in centipoises (i.e., cP).

The results of these assays are provided in FIG. 2. No decrease in the viscosity was observed over the course of the experiment for the Control, Host A (-bglC) and Host B (-bglC) samples contacted with the 1% cellulosic material, indicating the absence of cellulase activity in the samples. Host strains with deleted bglS genomic sequences exhibited significant cellulase activity as indicated by the decrease in viscosity.

Example 3

Construction of bglC::Spectinomycin Strains Producing Protease

The following strains were tested in this experiment, a *Bacillus subtilis* strain making subtilisin protease and the same strain with an insertional inactivation of bglC.

Strains to be tested were constructed as follows. SC6 strain (spoIIE, amyE, aprE Pxyl:comK) was transformed with chromosomal DNA from a subtilisin-producing strain. Transformants were selected on L agar plates containing chloramphenicol (5 micrograms/ml) and 1.6% skim milk. The presence of subtilisin was confirmed by halo production on plates containing skim milk. The resulting strain, MDT04-250, was transformed with chromosomal DNA from a strain with an insertional inactivation of the bglC gene, and transformants were selected on L agar plates containing spectinomycin (100 micrograms/ml). The new strain, MDT05-28, was confirmed to be resistant to chloramphenicol (5 micrograms/ml) and spectinomycin (100 micrograms/ml). The two strains were amplified for protease by growing them sequentially on L agar plates containing chloramphenicol (10 micrograms/ml) and then chloramphenicol (25 micrograms/ml). These amplified strains were grown in shake flasks containing 25 ml of LB (Difco), glucose (0.1%) and chloramphenicol (25 micrograms/ml) in a 250 mL baffled flask. Shake flasks were incubated at 37° C. with shaking at 280 rpm and at $OD_{550}$ of 0.8, 1 mL of culture was mixed with 0.5 ml 30% glycerol and frozen at −70° C. Thirty microliters of the thawed vials were used to inoculate 40 ml of FNII media in 250 ml flasks. Two flasks per strain were used. The shake flasks were incubated at 37° C. with shaking at 280 rpm for several days, and samples of the supernatant were collected for viscosity testing and subtilisin analysis.

Supernatants from liquid cultures were harvested after different times during growth (e.g., 16, 48 and 68 h) and assayed for subtilisin as previously described (See, Estell et al., J. Biol. Chem., 260:6518-6521 [1985]) in a solution containing 0.3 mM N-succinyl-L-Ala-L-Ala-L-Pro-L-Phe-p-nitroanalide (Vega Biochemicals), 0.1 M Tris, pH 8.6 at 25° C. The assays measured the increase in absorbance at 410 nm/min due to hydrolysis and release of p-nitroaniline. These strains produced equivalent amounts of subtilisin at equivalent rates.

Figure 3:
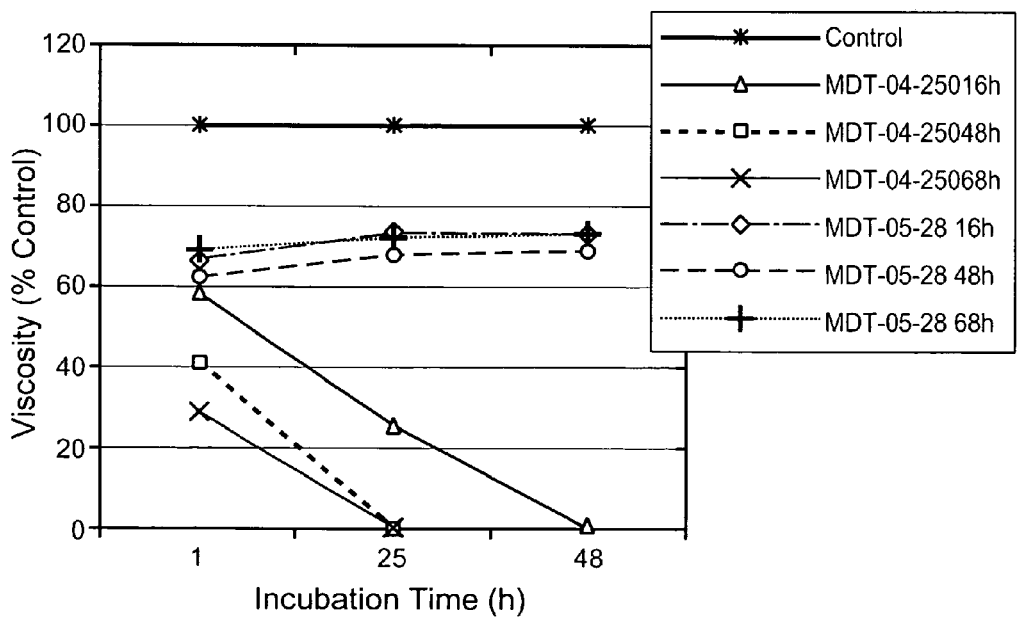
FIG. 3 is a graph showing the results of viscosity assays on the culture supernatants of two *Bacillus subtilis* strains producing recombinant subtilisin. Strain MDT-05-28 has an inactivated bglC gene whereas strain MTD-04-250 contains wild type bglC gene.

Supernatant samples from shake flasks of either the parent strain, MDT04-250 or the bglC::spec strain (MDT05-28) were taken at 16, 48 or 68 h after inoculation and incubated with a cellulose substrate (4.5 ml of 5% CMC+0.5 ml of supernatant) for 1, 24 or 48 h. The activity of cellulases on the cellulose substrate was measured by a drop in viscosity of the cellulose substrate as measured by a Rheometer using software as directed by the manufacturer, as discussed above. The data are presented as a percentage of the control ($dH_2O$) readings. Samples taken from the shake flasks of MDT05-28 did not show a reduction in viscosity of the cellulose substrate while all the samples from MDT04-250 quickly reduced the viscosity of the cellulose substrate. This indicates that the inactivation of bglC prevents activity on the cellulose substrate. The results of these assays are shown in FIG. 3. These results show that the culture supernatant from host *Bacillus* strains expressing subtilisin that have a disrupted bglC gene exhibit no significant cellulase activity.

While particular embodiments of the present invention have been illustrated and described, it will be apparent to those skilled in the art that various other changes and modifications can be made without departing from the spirit and scope of the invention. It is therefore intended to cover in the appended claims all such changes and modifications that are within the scope of this invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Having described the preferred embodiments of the present invention, it will appear to those ordinarily skilled in the art that various modifications may be made to the disclosed embodiments, and that such modifications are intended to be within the scope of the present invention.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

I claim:

1. A recombinant *Bacillus* sp. host cell comprising a genome comprising an inactivated bglC gene, wherein said cell further comprises a recombinant nucleic acid for production of a secreted detergent-additive protein.

2. The recombinant *Bacillus* sp. host cell of claim 1, wherein said inactivated bglC gene contains a deletion, an insertion, a substitution or a rearrangement.

3. The recombinant *Bacillus* sp. host cell of claim 1, wherein said *Bacillus* sp. cell is a *B. licheniformis*, *B. subtilis*, *B. clausii*, *B. alkalophilus* or *B. halodurans* cell.

4. The recombinant *Bacillus* sp. host cell of claim 1, wherein said secreted detergent-additive protein is an enzyme selected from a protease, an amylase, a pectate lyase, an acyltransferase, an arylesterase and a lipase.

5. The recombinant *Bacillus* sp. host cell of claim 4, wherein said enzyme is a protease.

6. The recombinant *Bacillus* sp. host cell of claim 5, wherein said protease is a subtilisin.

7. The recombinant *Bacillus* sp. host cell of claim 1, wherein said bglC gene encodes a polypeptide that is at least 80% identical to SEQ ID NO:2.

8. A culture of cells comprising:
culture medium; and
a recombinant *Bacillus* sp. host cell of claim 1.

9. A method, comprising:
maintaining the culture of cells of claim 8 under conditions suitable to produce said secreted detergent-additive protein.

10. The method of claim 9, further comprising:
recovering said secreted detergent-additive protein from said culture medium.

11. The method of claim 10, further comprising combining said secreted detergent-additive protein with a laundry detergent.

12. The method of claim 9, wherein said secreted detergent-additive protein is a subtilisin protease.

13. A cellulase-free protein composition produced by the method of claim 9.

14. The cellulase-free protein composition of claim 13, wherein said composition comprises a secreted detergent-additive protein produced by a *Bacillus* sp. and is characterized in that the composition is does not have detectable cellulase activity.

15. A cellulase-free laundry detergent comprising a secreted detergent-additive protein produced by the method of claim 9.

16. The cellulase-free laundry detergent of claim 15, wherein said detergent comprises a cellulosic polymer.

17. A method of making a cell, comprising:
a) introducing a first recombinant nucleic acid into a *Bacillus* sp. cell so that said recombinant nucleic acid recombines with the bglC gene of said cell; and
b) introducing a second recombinant nucleic acid into said cell that provides for expression of said secreted detergent-additive protein.

18. The method of claim 17 wherein said nucleic acid inserts into said bglC gene.

19. The method of claim 17, wherein said nucleic acid deletes at least a portion of said bglC gene.

20. The method of claim 17, wherein said secreted detergent-additive protein is a subtilisin.

* * * * *